United States Patent
Grunert et al.

(10) Patent No.: US 10,473,523 B2
(45) Date of Patent: Nov. 12, 2019

(54) APPARATUS FOR ILLUMINATING THE SURFACE OF A MATERIAL

(71) Applicant: PHOENIX CONTACT GMBH & CO KG, Blomberg (DE)

(72) Inventors: Fred Grunert, Bad Klosterlausnitz (DE); Fredrik Hailer, Weimar (DE); Thomas Nimz, Rothenstein (DE)

(73) Assignee: PHOENIX CONTACT GMBH & CO KG, Blomberg (DE)

(*) Notice: Subject to any disclaimer, the term of this patent is extended or adjusted under 35 U.S.C. 154(b) by 35 days.

(21) Appl. No.: 14/438,183

(22) PCT Filed: Oct. 23, 2013

(86) PCT No.: PCT/EP2013/072111
§ 371 (c)(1),
(2) Date: Apr. 23, 2015

(87) PCT Pub. No.: WO2014/067819
PCT Pub. Date: May 8, 2014

(65) Prior Publication Data
US 2015/0285681 A1  Oct. 8, 2015

(30) Foreign Application Priority Data
Oct. 31, 2012 (DE) .......................... 10 2012 110 429

(51) Int. Cl.
*G01J 3/02* (2006.01)
*G01J 3/10* (2006.01)
(Continued)

(52) U.S. Cl.
CPC ............. *G01J 3/0297* (2013.01); *G01J 3/027* (2013.01); *G01J 3/10* (2013.01); *G01J 3/42* (2013.01);
(Continued)

(58) Field of Classification Search
CPC .. G01J 3/42; G01J 3/027; G01J 3/0297; G01J 3/10; G01N 21/31; G01N 21/8806
See application file for complete search history.

(56) References Cited

U.S. PATENT DOCUMENTS

| | | | | |
|---|---|---|---|---|
| 7,045,757 B1 * | 5/2006 | Tuschel | ................... | G01J 3/02 250/208.1 |
| 7,342,214 B2 * | 3/2008 | Tuschel | ................... | G01J 3/10 250/208.1 |

(Continued)

FOREIGN PATENT DOCUMENTS

| | | |
|---|---|---|
| CN | 101072993 A | 11/2007 |
| CN | 101371114 A | 2/2009 |

(Continued)

OTHER PUBLICATIONS

International Searching Authority, "International Search Report" with English translation, issued in connection with application No. PCT/EP2013/072111, dated Jan. 20, 2014 (5 pages).

*Primary Examiner* — Violeta A Prieto
(74) *Attorney, Agent, or Firm* — Loeb & Loeb LLP

(57) ABSTRACT

An apparatus for illuminating the surface of a material, comprising an illuminating device for illuminating the surface of the material with a calibrating light, a recording device for recording a measuring light, emitted by the surface of the material in response to the calibrating light, and a processor device for recording the spectral characteristic of the measuring light that characterizes a diffuse spectral reflectance of the surface of the material, wherein the illuminating device is configured to generate an illuminating light for illuminating the surface of the material that has a spectral characteristic that corresponds to the spectral characteristic of the measuring light.

14 Claims, 1 Drawing Sheet

(51) Int. Cl.
    *G01J 3/42*     (2006.01)
    *G01N 21/31*     (2006.01)
    *G01N 21/88*     (2006.01)

(52) U.S. Cl.
    CPC ......... *G01N 21/31* (2013.01); *G01N 21/8806* (2013.01)

(56) References Cited

U.S. PATENT DOCUMENTS

| | | | |
|---|---|---|---|
| 7,433,034 B1 * | 10/2008 | Huang | G01N 21/94 356/237.5 |
| 7,465,911 B2 * | 12/2008 | Tuschel | G01J 3/10 250/208.1 |
| 2002/0024653 A1 * | 2/2002 | Jung | G01J 3/02 356/73 |
| 2003/0232445 A1 * | 12/2003 | Fulghum, Jr. | A61B 5/0071 436/63 |
| 2006/0000963 A1 | 1/2006 | Ng et al. | |
| 2006/0164657 A1 * | 7/2006 | Chalmers | G01B 11/0625 356/630 |
| 2006/0274301 A1 * | 12/2006 | Tuschel | G01J 3/10 356/73 |
| 2008/0093539 A1 * | 4/2008 | Tuschel | G01J 3/10 250/226 |
| 2008/0316475 A1 | 12/2008 | Fukazawa et al. | |
| 2009/0058999 A1 | 3/2009 | Gono et al. | |
| 2011/0026029 A1 * | 2/2011 | Iwasaki | G01J 3/02 356/417 |
| 2011/0295541 A1 | 12/2011 | Yu et al. | |
| 2013/0027702 A1 * | 1/2013 | Kawamata | G01J 3/457 356/326 |
| 2013/0100439 A1 * | 4/2013 | Yu | G01N 21/255 356/73 |
| 2014/0347676 A1 * | 11/2014 | Velten | G01B 11/2513 356/614 |
| 2015/0000384 A1 * | 1/2015 | Chekalyuk | G01N 21/6402 73/61.48 |
| 2017/0153142 A1 * | 6/2017 | Rosen | G01J 3/0275 |

FOREIGN PATENT DOCUMENTS

| | | | |
|---|---|---|---|
| DE | 10241472 A1 | 3/2004 | |
| JP | 08219716 A | 8/1996 | |
| JP | 11237344 A | 8/1999 | |
| JP | 05332939 B2 | 11/2013 | |
| WO | WO 2011126112 A1 * | 10/2011 | G01J 3/457 |

* cited by examiner

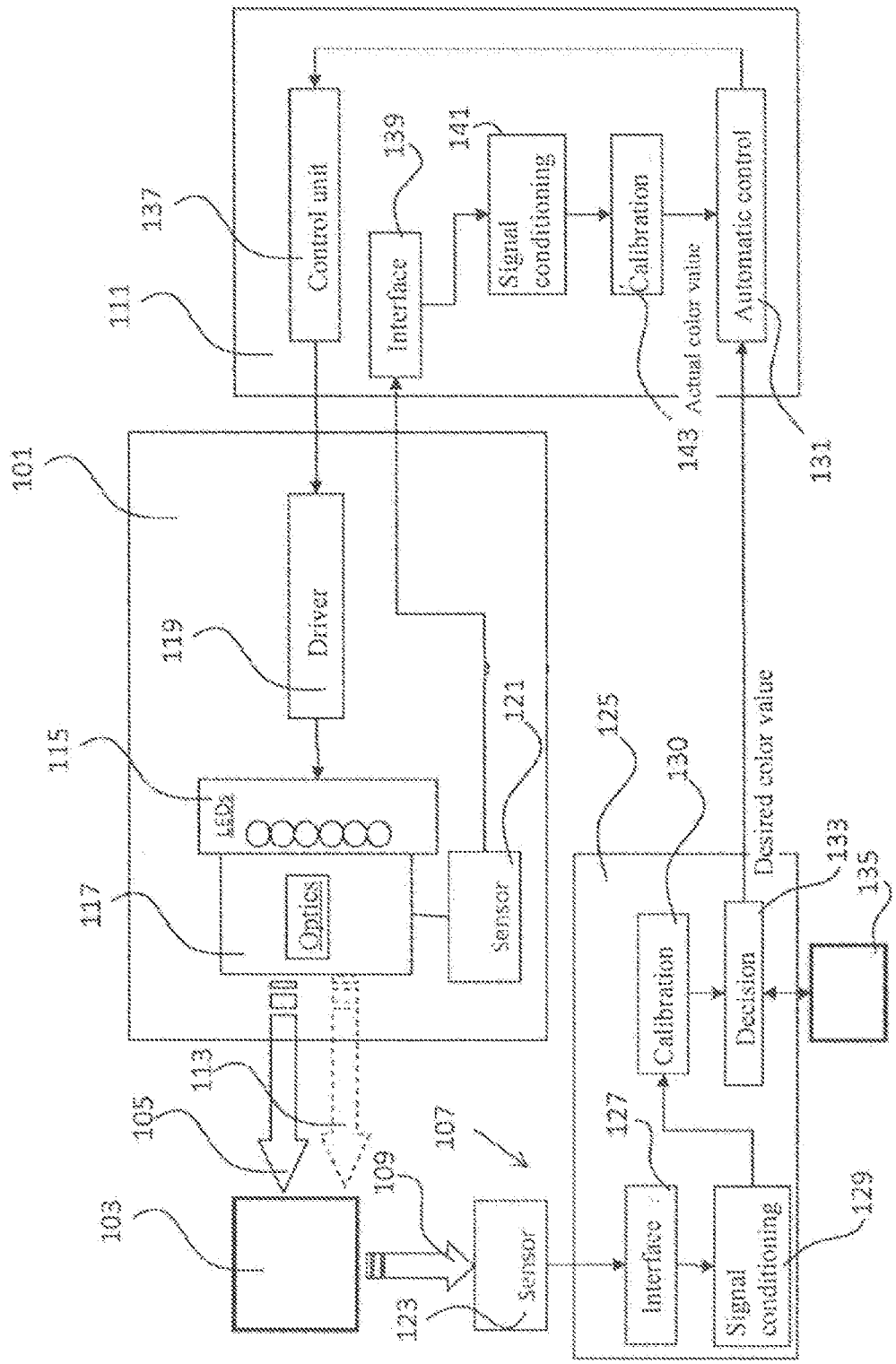

APPARATUS FOR ILLUMINATING THE SURFACE OF A MATERIAL

FIELD OF THE INVENTION

The present invention relates to the field of illuminating objects such as, for example, workpieces, for the optical detection of object detection.

RELATED TECHNOLOGY

In modern manufacturing installations, there is often the need for optical recording or detection of objects such as, for example, workpieces, products and the like. For this purpose, the surfaces of objects are usually illuminated with white light, wherein the light that is reflected by the surface of an object is optically recorded and optionally further conditioned in order to obtain an image of the object.

However, the optical recording and the analysis of the optically recorded image of the object can be disturbed by interfering light, for example, by ambient light such as hall illumination or by scattered light.

For this reason, there is a need to reduce the influence of interfering light in the optical recording of objects, particularly in manufacturing installations.

For this purpose it is indeed possible to increase the intensity of the object illumination. However, this can lead to the generation of additional interfering light, which can disturb, for example, adjacent optical recording operations. Another possibility for reducing the influence of the interfering light consists in optically recording the interfering light and reducing the intensity of the object illumination in the spectral range of the interfering light, in order to obtain a homogeneous illumination of the object. However, this is problematic particularly if the spectral intensity pattern of the interfering light is subject to temporal variations, which is the case, for example, with artificial illumination or at different times of the day.

SUMMARY

Therefore, the object of the present invention is to create an efficient concept for the illumination of surfaces of materials, wherein the influence of interfering light can be reduced.

This object is solved by the features of the independent claims. Advantageous variants are subject matter of the description, the drawings as well as the dependent claims.

The present invention is based on the finding that the above object can be solved by an adaptation of an illuminating light that is to be used for illuminating a surface of a material, for example, a surface of a workpiece.

For this purpose, the surface of the material is illuminated at least twice, wherein, in a first illumination process, the spectral remission behavior of the surface of the material is recorded. The spectral remission behavior of the surface of the material, which is characterized by a measuring light coming from the surface of the material, is used in order to adapt the illuminating light or the spectral characteristic thereof, in particular the color temperature, to the measuring light.

In this manner, the spectrum or the color composition of the illuminating light to be used for illuminating the surface of the material is adapted to the optical properties of the surface of the material. If the surface of the material is characterized, for example, by a stronger intensity of the reflected light in a first spectral range than in a second spectral range, then the intensity of the illuminating light in the first spectral range can be higher than the intensity of the illuminating light in the second spectral range. In this manner, the surface of the material is spectrally illuminated with a greater intensity at the site where a stronger response intensity should be expected. On the other hand, if the surface of the material absorbs light of a certain wavelength, then it is possible, for example, to dispense with the illumination of the surface of the material at this wavelength. This leads to a more energy-efficient illumination of surfaces of materials.

According to one aspect, the invention relates to an apparatus for illuminating a surface of a material, comprising an illuminating device for illuminating the surface of the material by means of a calibrating light, a recording device for recording a measuring light emitted by the surface of the material in response to the calibrating light, and a processor device for recording the spectral characteristic of the measuring light, which characterizes a spectral remission behavior of the surface of the material; wherein the illuminating device is configured to generate an illuminating light for illuminating the surface of the material, which has a spectral characteristic that corresponds to the spectral characteristic of the measuring light.

According to an implementation form, the measuring light is a light reflected on the surface of the material in response to the calibrating light, or a light reemitted by the surface of the material in response to the calibrating light, or a light emitted by the surface of the material in response to the calibrating light.

According to an implementation form, the spectral characteristic of the measuring light is a color spectrum of the measuring light in accordance with a color space, a wavelength spectrum of the measuring light, or a frequency spectrum of the measuring light.

According to an implementation form, the illuminating device is configured to generate the illuminating light with a spectral characteristic that corresponds to, in particular is equal to, the spectral characteristic of the measuring light within a tolerance range, for example, 1%, 5% or 10%.

According to an implementation form, the processor device is configured to transfer an indication on the spectral characteristic of the measuring light to the illuminating device. As a result, the illuminating device can be controlled, for example, so as to generate the desired illuminating light.

According to an implementation form, the processor device is configured to control the illuminating device for adjusting the spectral characteristic of the illuminating light in dependence of the spectral characteristic, in particular in accordance with the spectral characteristic, of the measuring light.

According to an implementation form, the illuminating device comprises a plurality of light elements for emitting light of different wavelengths or different colors.

According to an implementation form, the illuminating device is configured to control at least one light element of the plurality of light elements, in particular each light element of the plurality of light elements, for emitting light of a predetermined intensity, in order to adjust the spectral characteristic of the illuminating light.

According to an implementation form, the processor device is configured to record a characteristic of the surface of the material on the basis of the measuring light.

According to an implementation form, the recording device comprises an optical sensor for recording the measuring light.

According to an implementation form, the illuminating device comprises an optical sensor for recording an actual illuminating light, wherein the processor device is configured to record a difference between a spectral characteristic of the actual illuminating light and a spectral characteristic of a desired illuminating light, and to control the illuminating device in dependence of the difference. As a result, the illuminating light can be adjusted with automatic control.

According to an implementation form, the recording device is configured to record an image light emitted by the surface of the material in response to the illuminating light.

According to an implementation form, the processor device is configured to convert the image light into a test image, in particular into a digital test image.

According to an additional aspect, the invention relates to a method for illuminating a surface of a material, with an illumination of the surface of a material with the calibrating light, a recording of a measuring light emitted by the surface of the material in response to the calibrating light, which characterizes a spectral remission behavior of the surface of the material, a recording of a spectral characteristic of the measuring light, and an illumination of the surface a material with an illuminating light which has a spectral characteristic that corresponds to the spectral characteristic of the measuring light.

BRIEF DESCRIPTION OF THE DRAWINGS

Additional implementation forms are described in reference to FIG. 1, which shows a block diagram of an apparatus for illuminating a surface of the material.

DETAILED DESCRIPTION

FIG. 1 shows a block diagram of an apparatus for illuminating a surface of the material 103, with an illuminating device 101 for illuminating the surface of the material 103 by means of a calibrating light 105, and with a recording device 107 for recording a measuring light 109 emitted by the surface of the material 103 in response to the calibrating light 105. The measuring light can be, for example, light reflected on the surface of the material 103 or light emitted or reemitted by the surface of the material 103.

Furthermore, a processor device 111 is provided, which is configured to record a spectral characteristic, for example, a color composition or a wavelength pattern, of the measuring light 109. The spectral characteristic of the measuring light 109 characterizes, in particular, the spectral remission behavior of the surface of the material. The measuring light can be, for example, reflected light, reemitted light or emitted light.

The illuminating device 101 is configured to generate an illuminating light 113 for illuminating the surface of the material, which has a spectral characteristic that corresponds to the spectral characteristic of the measuring light.

The illuminating process is thus a two-step process. In the first step, the illuminating device 101 generates the measuring light 105. After the recording of the spectral characteristic of the measuring light 105, the surface of the material 103 is illuminated with an illuminating light 113 whose spectrum corresponds to the spectrum of the measuring light, within a tolerance, for example, 5% or 10%. Therefore, the measuring light 105 is generated first. The illuminating light 113 is generated temporally after the generation of the measuring light 105.

The illuminating device 101 comprises a plurality of light elements 115, which are provided for emitting the calibrating light and/or the illuminating light. The light elements 115 can be, for example, light emitting diodes (LED), each of which emits light of a different color, for example, red, green or yellow, or of another wavelength. By energizing the individual light elements 115, a predetermined color composition or spectral characteristic of the illuminating light can be generated.

An optics unit 117, for example, a lens, can optionally be connected downstream of the light elements 115, for example, in order to focus the emitted light.

For driving the light elements 115, a driver 119, for example, an LED driver, is provided, which is connected upstream of the light elements 115.

According to an implementation form, the driver 119 is an element of the illuminating device 101. According to another implementation form, the driver 119 is an element of the processor device 111.

The illuminating device 101 comprises a sensor 121 which is provided for recording the light generated by the lighting elements 115, optionally after the optics unit 117, as actual light, in particular as actual illuminating light, and for applying a corresponding measurement signal to the processor device 111 for the automatic control of the control system of the illuminating device 101.

The illuminating device 101 is provided in order to emit, by means of the lighting elements 115, both the calibrating light 105, for the calibration of the system to the surface of the material, and also the illuminating light 113 in the direction of the surface of the material 103, which characterizes the spectral light behavior of the surface of the material.

The light emitted or reflected by the surface of the material 103 in response to the calibrating light or illuminating light is recorded by the recording device 107. For this purpose, the recording device 107 comprises an optical sensor 123, which optically records the light 109 emitted by the surface of the material 103. An output signal of the optical sensor 123 is applied to a control unit 125.

In accordance with an implementation form, the control unit 125 is an element of the recording device 107. According to another implementation form, the control unit 125 is an element of the processor device 111.

The control unit 125 comprises an interface 127 which can be digital and which can be configured, for example, as a 120, SPI, USB or a similar interface.

The interface 127 can comprise an analog-digital converter, for example. This is advantageous if the optical sensor 123 converts the recorded light into an analog measurement signal. If the optical sensor 123 is provided in order to convert the recorded light into a digital signal, then the interface 127 can be an I2C, SP or a USB interface, for example.

Arranged downstream of the interface 127 is a signal conditioning device 129 which carries out, for example, a filtering of an output signal of the interface 127. The filtering can produce, for example, a signal smoothing. The signal smoothing can be dependent on a frequency or wavelength of the recorded or measured light.

The control unit 125 moreover comprises an optional calibration device 130 which is provided in order to receive the conditioned signal data from the signal conditioning device 129 and calibrate the data. Here, the conditioned signal data can be calibrated, for example, in terms of the color value according to a color space.

The output data of the calibration device 130 can be applied according to an implementation form to the processor device 111, in particular to an automatic control device 131 of the processor device 111.

According to an implementation form, the output data of the calibration device 130 can be applied to an optional decision device 133.

According to an implementation form, the decision device 133 can perform, for example, an edge detection in a digital image, for example, in order to detect contours of the illuminated object with the material surface.

According to an implementation form, the decision device 133 can associate the spectral characteristic of the light, which is emitted by the surface of the material 103 in response to the calibrating light or illuminating light and recorded, with actual color values, which can define not only the spectral characteristic of the measuring light, but also the spectral characteristic of the illuminating light to be used. In this manner, the illuminating device 101 can be controlled automatically for generating a desired illuminating light.

For this purpose, the processor device 111 comprises a control unit 137, for example, an LED control unit, which controls the driver 119 in accordance with the desired color values of a desired illuminating light, for generating an illuminating signal. For this purpose, the control unit 137 can be configured in order to control the lighting elements 1115 associated with respective colors, for example, individually, in order to obtain the spectral characteristic of the illuminating light in accordance with the spectral characteristic of the measuring light or the desired color values.

Optionally, the automatic control device 131 can be provided in order to adjust the lighting elements 1115 in the case of a deviation between the desired illuminating signal and an actual illuminating signal, so that, for example, a difference between the desired illuminating signal and the actual illuminating signal, in particular a spectral difference, can be reduced.

For this purpose, the processor device 111 can be configured so as to obtain a measurement signal from the sensor 121, which represents the actual illuminating signal. The sensor 121 can be an optical sensor which converts visible light into an analog or into a digital measurement signal. The processor device 111 can comprise an interface 139 for receiving a measurement signal from the sensor 121, interface which can be digital and configured, for example, which can be digital and which can be configured, for example, as a 120, SPI, USB or as a similar interface.

The interface 139 can comprise, for example, an analog-digital converter and/or be a 120, SBI or USB interface. Connected downstream of the interface 139 is an optional signal conditioning 141, which can have the functionality of the signal conditioning 129 of the control unit 125. The signal conditioning 129 can perform, for example, a signal smoothing, for example, in dependence of a frequency of the measured light.

An optional calibration device 143, which carries out a correction of the conditioned signal data in terms of color value, is connected downstream of the signal conditioning device 141. The calibration device 143 can have the functionality of the calibration device 130. The calibration device 143 is provided, in particular, for applying an actual color value, which characterizes the spectral characteristic of the actual illuminating signal, to the automatic control device 131. The automatic control device 131 is configured, for example, to determine a deviation between the actual color value and the desired color value, and to issue, on this basis, an actuating variable for the control unit 137, in order to control the driver 119 for driving the lighting elements 115.

According to an implementation form, the control unit 137, the interface 139, the signal conditioning device 141, the calibration device 143 as well as the automatic control device 131 can be implemented by means of a microcontroller.

LIST OF REFERENCE NUMERALS

101 Illuminating device
103 Surface of the material
105 Calibrating light
107 Recording device
109 Measuring light
111 Processor device
113 Illuminating light
115 Light element
117 Optics
119 Driver
121 Optical sensor
123 Optical sensor
125 Control unit
127 Interface
129 Signal conditioning device
130 Calibration device
131 Automatic control device
133 Decision device
135 Display
137 Control unit
139 Interface
1115 Lighting element
141 Signal conditioning
143 Calibration device

The invention claimed is:

1. An apparatus for reducing an influence of interfering light to illuminate a surface of a material with an illuminating light, the apparatus comprising:

a light source configured to illuminate the surface of the material with a calibrating light, wherein the light source comprises lighting elements and a sensor, the lighting elements provided for emitting the calibrating light and the illuminating light, and the sensor provided for recording the light generated by the lighting elements as actual light;

a detector configured to record a measuring light emitted by the surface of the material in response to the calibrating light and in the presence of interfering light; and a processor configured to:
cause the detector to record a spectral characteristic of the measuring light, which characterizes a spectral remission behavior of the surface of the material;
cause the light source to generate the illuminating light for illuminating the surface of the material in the presence of the interfering light after recording the spectral characteristic of the measuring light,
automatically adjust the spectral characteristic of the illuminating light in dependence of the spectral characteristic of the measuring light recorded by the detector;

wherein the spectral characteristic of the illuminating light corresponds to the spectral characteristic of the measuring light, and the interfering light is ambient light, which originates from outside of the apparatus;

wherein the processor is configured to obtain a measurement signal from the sensor, the measurement signal including an actual illumination signal, and wherein the processor comprises a controller to adjust the lighting elements in the case of a deviation from a desired illumination signal and the actual illumination signal.

2. The apparatus according to claim 1, wherein the measuring light is
- a light reflected on the surface of the material in response to the calibrating light, or
- a light reemitted by the surface of the material in response to the calibrating light, or
- a light emitted by the surface of the material in response to the calibrating light.

3. The apparatus according to claim 1, wherein the spectral characteristic of the measuring light is
- a color spectrum of the measuring light according to a color space,
- a wavelength spectrum of the measuring light, or
- a frequency spectrum of the measuring light.

4. The apparatus according to claim 1, wherein the light source is configured to generate the illuminating light with a spectral characteristic that corresponds to, in particular is equal to, the spectral characteristic of the measuring light within a tolerance range.

5. The apparatus according to claim 1, wherein the processor is configured to transfer an indication on the spectral characteristic of the measuring light to the light source.

6. The apparatus according to claim 1, wherein the light source emits the calibrating light in a first wavelength and the illuminating light in a second wavelength.

7. The apparatus according to claim 1, wherein the lighting elements are light emitting diodes.

8. The apparatus according to claim 1, wherein the light source is configured to control at least one light element of the lighting elements, in particular each light element of the lighting elements, for emitting light of a predetermined intensity, in order to adjust the spectral characteristic of the illuminating light.

9. The apparatus according to claim 1, wherein the processor is configured to record a characteristic of the surface of the material on the basis of the measuring light.

10. The apparatus according to claim 1, wherein the detector comprises an optical sensor for recording the measuring light.

11. The apparatus according to claim 1, wherein the processor is further configured to record a difference between a spectral characteristic of the actual illuminating light and a spectral characteristic of a desired illuminating light, and is further configured to control the light source in dependence of the difference.

12. The apparatus according to claim 1, wherein the detector is configured to record an image light emitted by the surface of the material in response to the illuminating light.

13. The apparatus according to claim 12, wherein the processor is further configured to convert the image light into a test image.

14. A method for reducing an influence of interfering light to illuminate a surface of a material with an illuminating light, the method comprising:
- illuminating the surface of the material with a calibrating light;
- recording a measuring light emitted by the surface of the material in response to the calibrating light and in the presence of interfering light;
- recording a spectral characteristic of the measuring light, which characterizes a spectral remission behavior of the surface of the material;
- automatically adjusting the spectral characteristic of the illuminating light in dependence of the recorded spectral characteristic of the measuring light;
- illuminating the surface of the material with the illuminating light in the presence of interfering light after recording the spectral characteristic of the measuring light, the illuminating light having a spectral characteristic that corresponds to the spectral characteristic of the measuring light, wherein the interfering light is ambient light, which originates from outside of an apparatus for illuminating the surface of the material in accordance with the method;
- obtaining a measurement signal from a sensor recording the illuminating light, which represents an actual illumination signal; and
- adjusting the illuminating light in the case of a deviation from a desired illumination signal and the actual illumination signal.

* * * * *